US006371924B1

(12) United States Patent
Stearns

(10) Patent No.: US 6,371,924 B1
(45) Date of Patent: Apr. 16, 2002

(54) ACOUSTIC WINDOW IDENTIFICATION

(75) Inventor: Scott Donaldson Stearns, Rochester, NY (US)

(73) Assignee: MedAcoustics, Inc., Raleigh, NC (US)

(*) Notice: Subject to any disclaimer, the term of this patent is extended or adjusted under 35 U.S.C. 154(b) by 0 days.

(21) Appl. No.: 09/433,211

(22) Filed: Nov. 4, 1999

Related U.S. Application Data
(60) Provisional application No. 60/107,616, filed on Nov. 9, 1998.

(51) Int. Cl.[7] .................................................. A61B 5/02
(52) U.S. Cl. ...................................................... 600/528
(58) Field of Search ................................. 600/511, 514, 600/520, 508, 527–528, 586, 310, 450, 407, 437

(56) References Cited

U.S. PATENT DOCUMENTS

| 4,008,408 A | 2/1977 | Kodama |
| 4,183,249 A | 1/1980 | Anderson |
| 4,268,912 A | 5/1981 | Congdon |
| 4,308,870 A | 1/1982 | Arkans |
| 4,509,527 A | 4/1985 | Fraden |

(List continued on next page.)

FOREIGN PATENT DOCUMENTS

| GB | 2166871 A | 5/1986 |
| WO | WO/90-08506 | 9/1990 |

OTHER PUBLICATIONS

Durand et al.: Spectral analysis and acoustic transmission of mitral and aortic closure sounds in dogs Medical & Biological Engineering and Computing 28:4 269–277 (1990).*
Durand, et al.: "Spectral analysis and acoustic transmission of mitral and aortic valve closure sounds in dogs" *Medical & Biological Engineering & Computing* 28:4 269–277 (1990).

International Search Report for PCT US 99/26198; mailed May 2, 2000.
Akay et al., "Noninvasive acoustical detection of coronary artery disease using the adaptive line enhancer method," Medical & Biological Engineering & Computing, vol. 30, pp. 147–154 (Mar. 1992).
Akay et al., "Noninvasive Acoustical Detection of Coronary Artery Disease: A Comparative Study of Signal Processing Methods," IEEE Transactions on Biomedical Engineering, vol. 40, No. 6, pp. 571–5784 (Jun. 1993).
Donnerstein, "Continuous Spectral Analysis of Heart Murmurs for Evaluating Stenotic Cardiac Lesions," The Am. Journ. Card., vol. 64, pp. 625–630 (Sep. 15, 1989).
Durand et al., "Spectral Analysis and Acoustic Transmission of Mitral nd Aortic Valve Closure Sounds In Dogs," Med. Bio. Comp., vol. 28, No. 4 (Jul. 1990).
Fraden, "Application of Piezo/Pyroelectric Films in Medical Transducers," Jour. of Clinical Eng., vol. 13, No. 3, pp. 133–138 (Mar.–Apr. 1988).
Semmlow et al., Noninvasive Detection of Coronary Artery Disease Using Parametric Spectral Analysis Methods, *IEEE Engineering in Medicine and Biology Magazine*, pp. 33–36 (Mar. 1990).
Stein et al., "Frequency Spectra of the First Heart Sound and of the Aortic Component of the Second Heart Sound in Patients with Degenerated Porcine Bioprosthetic Valves," The Am. Journ. of Carad., vol. 53, pp. 557–581 (Feb. 1, 1984).

Primary Examiner—George R. Evanisko
(74) Attorney, Agent, or Firm—Myers Bigel Sibley & Sajovec, P.A.

(57) ABSTRACT

Methods for identifying and/or visualizing an acoustic window suitable for passive acoustic coronary heart disease evaluations by mapping the relative SNR distribution on the channels on an array of a plurality of sensors to nominal locations on a person's chest of each sensor in the acoustic sensor array and identifying a plurality of sensor locations that correspond to the highest channel SNR's is described and/or sizing the acoustic sensor array to correspond with the identified acoustic window.

14 Claims, 8 Drawing Sheets

U.S. PATENT DOCUMENTS

| | | |
|---|---|---|
| 4,777,961 A | 10/1988 | Saltzman |
| 5,035,247 A | 7/1991 | Heimann |
| 5,036,857 A | 8/1991 | Semmlow et al. |
| 5,086,776 A | 2/1992 | Fowler, Jr. et al. |
| 5,140,992 A | 8/1992 | Zuckerwar et al. |
| 5,337,752 A | 8/1994 | Reeves |
| 5,365,937 A | 11/1994 | Reeves et al. |
| 5,394,876 A | 3/1995 | Ma |
| 5,551,437 A | 9/1996 | Lotscher |
| 5,598,845 A | 2/1997 | Chandraratna et al. |
| 5,727,561 A | 3/1998 | Owsley |
| 5,785,657 A | 7/1998 | Breyer et al. |
| 5,807,268 A | 9/1998 | Reeves et al. |
| 5,853,005 A | 12/1998 | Scanlon |
| 6,193,668 B1 | 2/2001 | Chassaing et al. |

\* cited by examiner

ACOUSTIC WINDOW IDENTIFICATION

RELATED APPLICATIONS

This application claims priority from U.S. Provisional Application No. 60/107,616 filed on Nov. 9, 1998. The contents of this application are hereby incorporated by reference herein. This application is related to co-pending and co-assigned U.S. patent application Ser. No. 09/188,510, entitled "Non-Invasive Turbulent Blood Flow Imaging System," filed Nov. 9, 1998, which corresponds to PCT/US97/20186 filed Nov. 10, 1997 ("the 20186 application"). This application is also related to co-pending and co-assigned U.S. patent application No. 09/188,434, entitled "Acoustic Sensor Array for Non-Invasive Detection of Coronary Artery Disease." This application is also related to co-pending and co-assigned U.S. patent application Ser. No. 09/136,933, entitled "Thin Film Piezoelectric Polymer Sensor". The contents of the above-identified applications are hereby incorporated by reference as if recited in full herein.

FIELD OF THE INVENTION

This invention relates to the non-invasive detection of abnormal blood flow sounds by an array of acoustic sensors.

BACKGROUND OF THE INVENTION

The 20186 application describes an invention for the non-invasive in vivo detection and localization of abnormal blood flow. Embodiments of that invention entail display of the spatial distribution of phase coherence in the shear wave component blood flow signals generated by an acoustic sensor array. An essentially uniform display indicates normal blood flow. A non-uniform display may indicate the presence of an occlusion and the presence or extent of abnormal, turbulent blood flow. Poor correlation of signals from the array sensors may adversely affect the display uniformity.

Acoustic sensor arrays may be positioned above a measurement area defined as the (hairless) human chest skin located vertically between the sternum and a parallel line passing through the left nipple and horizontally 10 cm above and 6 cm below the left and right nipples.

A prior art acoustic sensor array comprising eight equally spaced sensors in two concentric circles having prime numbers of sensors in each circle and a ninth sensor at the common center of the concentric circles is illustrated by FIG. 6 of the 20186 application.

In operation, in order to reach sensors in a conventionally positioned prior art array as described in the 20186 application, sound waves must travel either directly through lung tissue or first to the body surface and then laterally with consequent attenuation of correlation. A study of the correlation by that array of patient data signals generated by the quiet interval has revealed that only four or five of the nine sensors are suitably or well correlated.

It is known that a notch ("cardiac notch") in the human left lung allows the heart to be in contact with the chest wall. Well correlated blood flow signals may be generated by acoustic sensors positioned on a human chest in a small area ("acoustic window") located above the cardiac notch. The bounds of the acoustic window have been approximated by ultrasonic probe means as described in the "Sensor Array" application.

However, there remains a need to be able to provide improved ways to identify the acoustic window for improved sensor operation and/or clinical applications.

SUMMARY OF THE INVENTION

The present invention employs a method for determining an acoustic window suitable for passive-acoustic coronary artery disease evaluation which includes the steps of (a) positioning a multi-channel acoustic sensor array (preferably having at least four and more preferably about 9–45 sensors) onto the chest of a subject; (b) calculating a weighted value for each of the sensor channels in the multi-channel sensor array; (c) determining the location of each sensor channel in the array; (d) identifying the sensor channels which meet predetermined test criteria; and (e) defining a perimeter which substantially extends about and encloses therewithin the sensor channels identified in step (d), thereby defining an acoustic window suitable for acoustic listening diagnostic procedures.

In a preferred embodiment the calculating step is performed by assigning signal to noise ratio (SNR) based weighted values to each of the sensor channels and the predetermined test criteria includes identifying the sensors exhibiting the three highest calculated weighted values or identifying at least three sensors exhibiting one or more high weight values. The acoustic window can be used to define one or more standard optimum sensor array geometry and sizes.

This invention involves the discovery that an acoustic window can be visualized by grayscale or equivalent mapping of optimal weights scaled to the estimated SNR on each of a plurality of channels of a multichannel acoustic sensor array to the nominal location of each sensor. The grayscale maps identify channels that achieve the highest SNR because the optimal weights represent a measure of the relative SNR distributed at each of the nominal sensor locations.

In operation, as shown in FIG. 7, the bounds of an acoustic window are visualized or defined by a perimeter (shown in dotted line) that encloses three or more channels that exhibit the highest relative SNR as measured by the optimal weights. The acoustic window is used to bound the aperture of an acoustic sensor array. This acoustic window identification increases or enhances the probability of acquiring the highest possible SNR on the largest percentage of sensors in the array.

DEFINITIONS

Weight—For the purposes of this invention a "weight" is a constant applied to the SNR on single sensor channel as indicative of its relative importance among all involved channels. An algorithm for computing the weights, and preferably the optimal weights for each channel scaled to the estimated SNR thereon is described in the 20186 application, and herein at Appendix A. The algorithm operationally corresponds to and/or depends on having the same sensor location in all measurements for a particular person.

Sensor or Accelerometer—Any current or voltage mode device which generates an electric signal from displacement or a derivative thereof upon detection of a sound wave.

Sensor Array—A pattern or spaced arrangement of a plurality of sensors on or to be placed on the body surface of a patient. For the purposes of this invention an array comprises four or more sensors.

Sensor Array Aperture—The space or area within the perimeter of an array where heart or blood flow sounds are detected by a sensor(s) positioned therein.

Sensor Array Geometry—The shape of the perimeter of a sensor array.

Channel—The path followed by a signal from a sensor by which the signal is generated to a receiver. A sensor array includes multiple sensors and multiple channels.

DETAILED DESCRIPTION OF PRFERRED EMBODIMENTS

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. In the figures, certain layers, regions, or components may be exaggerated or enlarged for clarity.

The invention comprises means for identifying or visualizing an acoustic window by mapping (relationally determining the position of) the nominal sensor locations of the weights associated with each sensor channel, and more preferably to optimal weights scaled to the estimated SNR on each of at least four channels of an acoustic sensor array.

Figure 7:
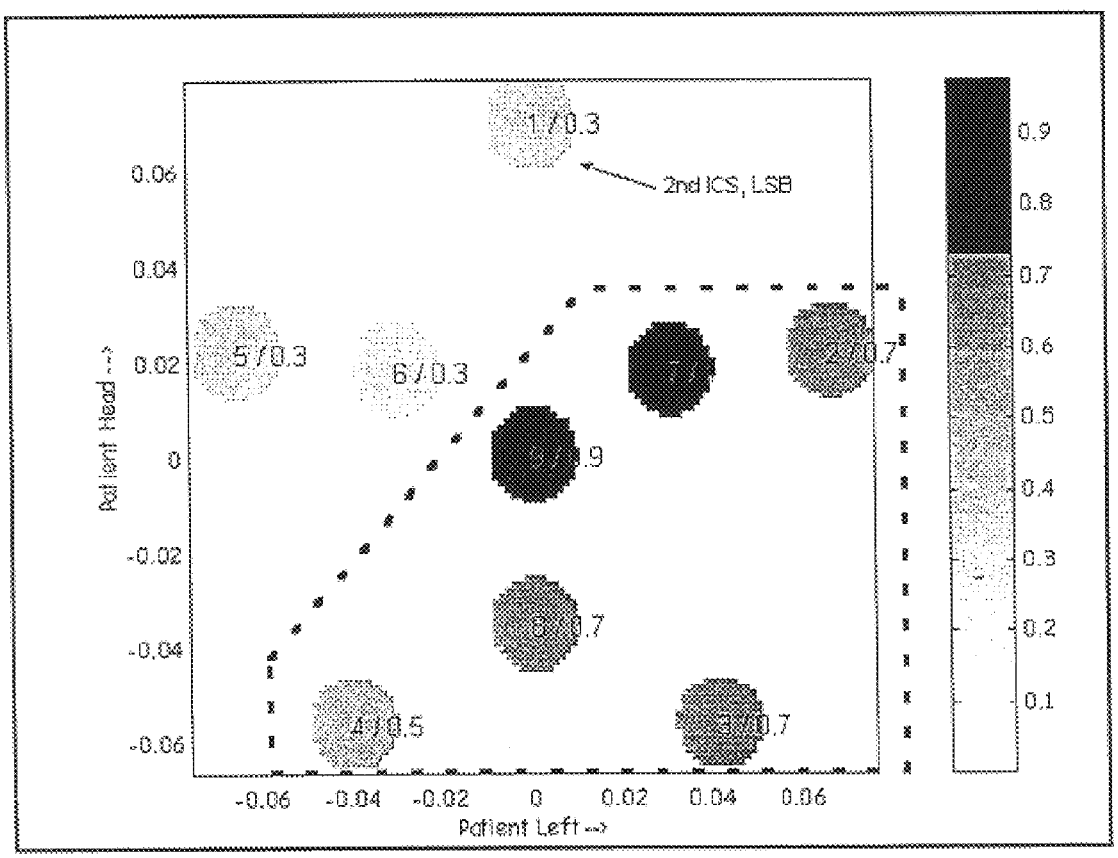
FIG. 7 is a duplicate of FIG. 1 upon which a broken line has been interposed to provide visualization of an acoustic window including sensors 4 to 9 assigned the highest optimal weights according to the present invention.

As shown in FIG. 7, the bounds of the acoustic window are visualized by a perimeter which encloses at least the three nominal sensor locations that correspond to the highest optimal channel weights. Any array that comprises four or more sensors, and therefore, four or more channels, may be used to practice the invention. Preferably, the sensor arrays used according to the present invention are configured to have from about 9 to 45 channels and preferably from 9–45 corresponding sensors.

Figure 1:
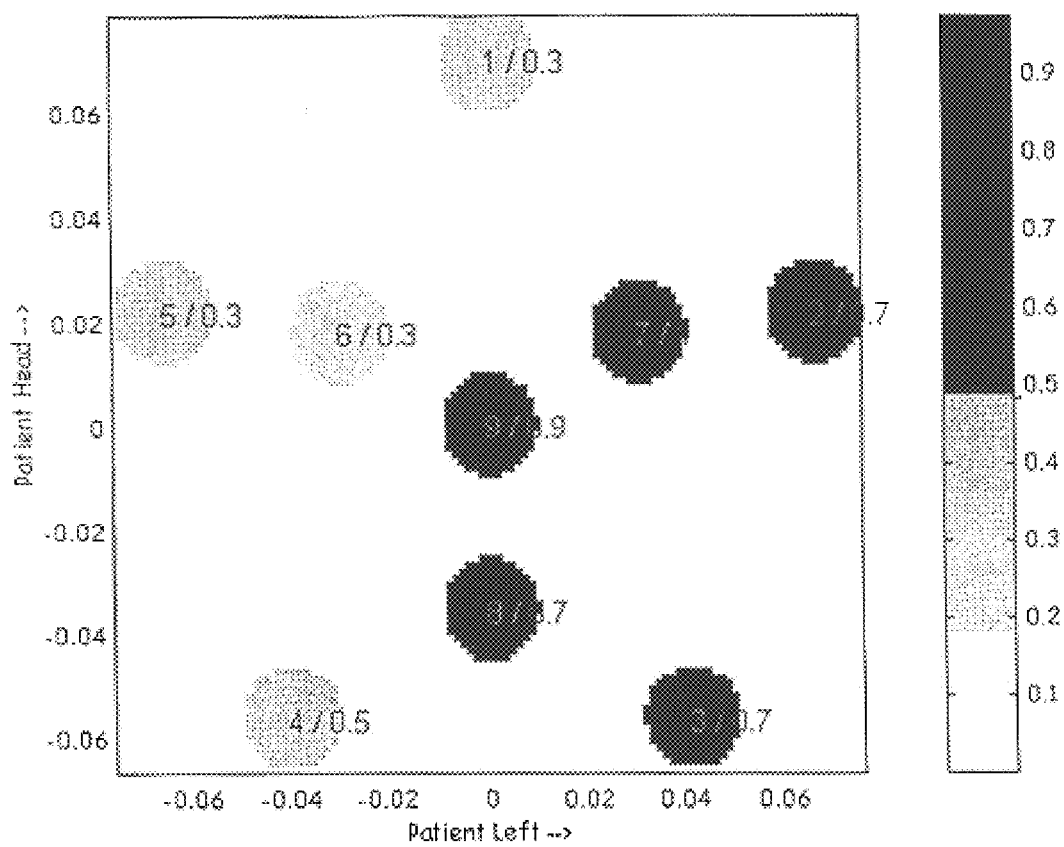
FIG. 1 is an image or display that depicts optimal weights scaled to the estimated channel SNR grayscale mapped to nine sensors in a conventional nine-sensor array as observed with a human patient. The sensors and corresponding channel are numbered 1 to 9. Maximum channel weights (the darker grayscale images) are shown for the sensors in the center and to the patient's left.
Figure 2:
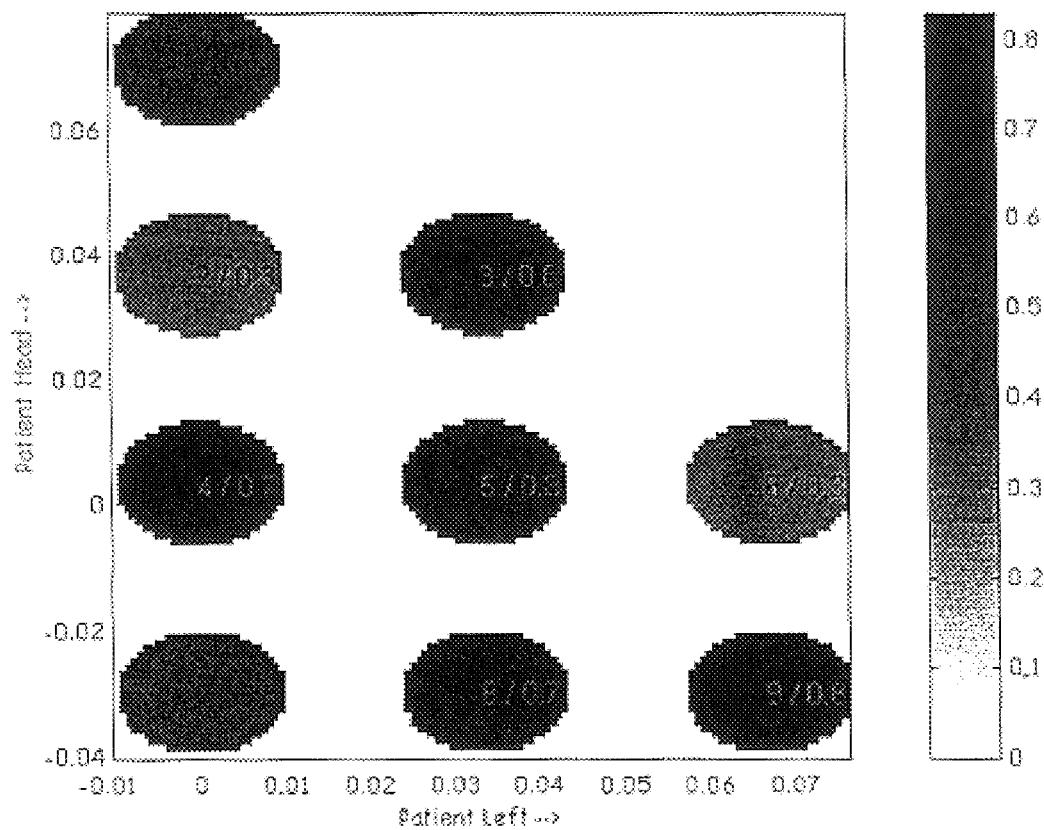
FIG. 2 is an image or display that depicts optimal weights scaled to the estimated channel SNR grayscale mapped to a nine-sensor array having the pattern indicated as observed with a human patient. The channel numbers and associated channel optimal weights are superimposed on the grayscale images, e.g., 1/0.4.
Figure 3:
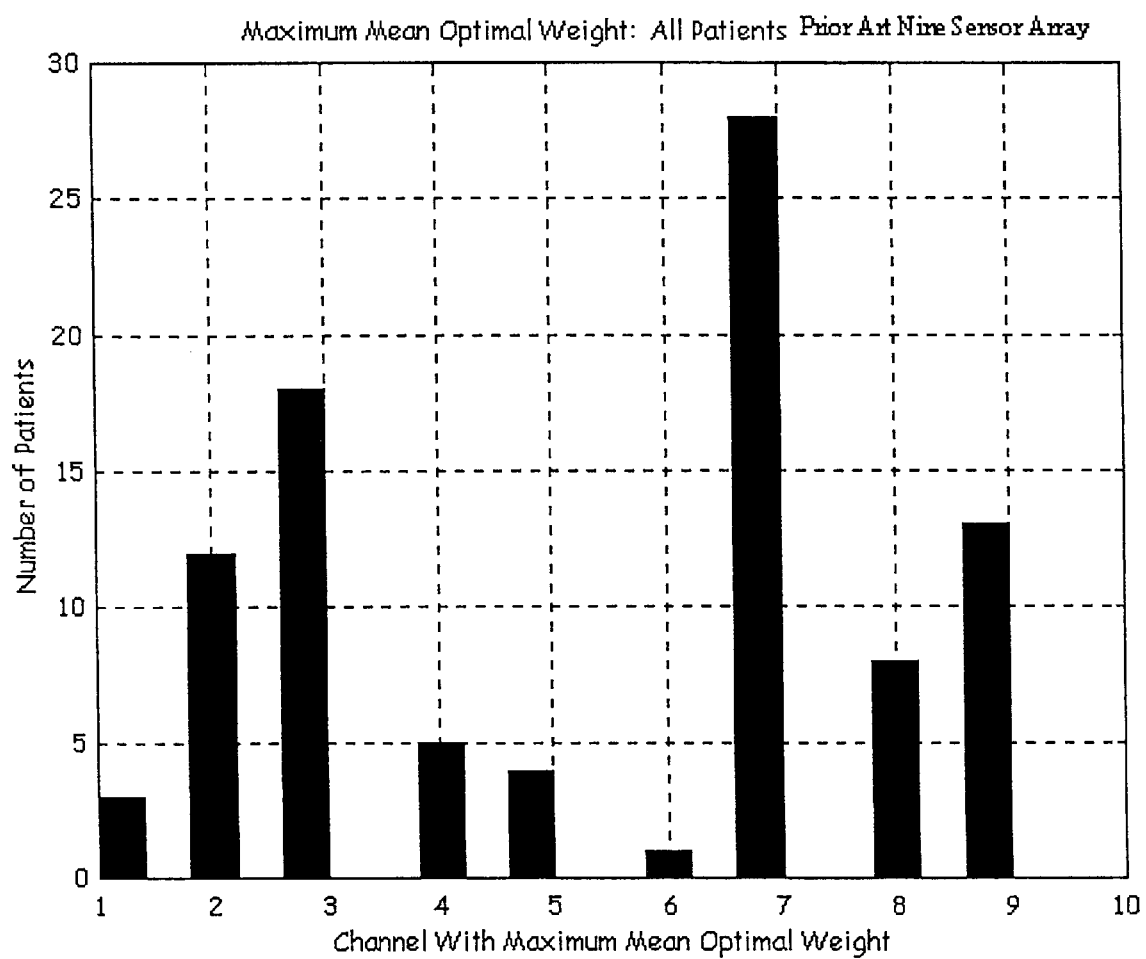
FIG. 3 is a histogram graph indicating the distribution of channels with maximum (highest relative SNR) mean optimal weight. The graph represents the maximum mean optimal weight for each channel across a population of patients (taken from about 100 intervention and non-intervention or not significantly diseased (NSD) patients) using the FIG. 1 conventional nine-sensor array configuration.
Figure 4:
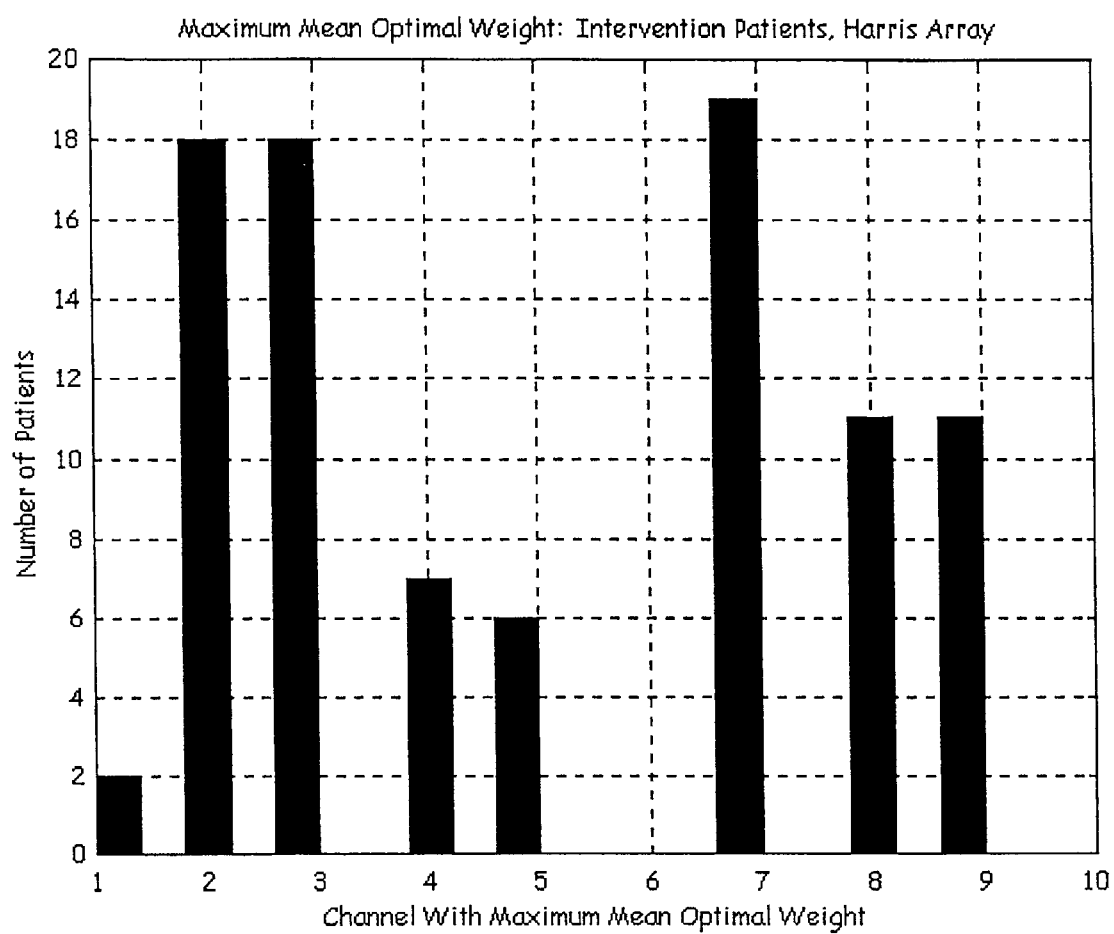
FIG. 4 is a histogram graph including indicating the distribution of channels with maximum mean (highest relative SNR) optimal weights. This graph represents the weights and channel distribution for intervention patients only (using the FIG. 1 conventional nine-sensor array configuration). The results are similar to that illustrated by FIG. 3 for all patients.
Figure 5:
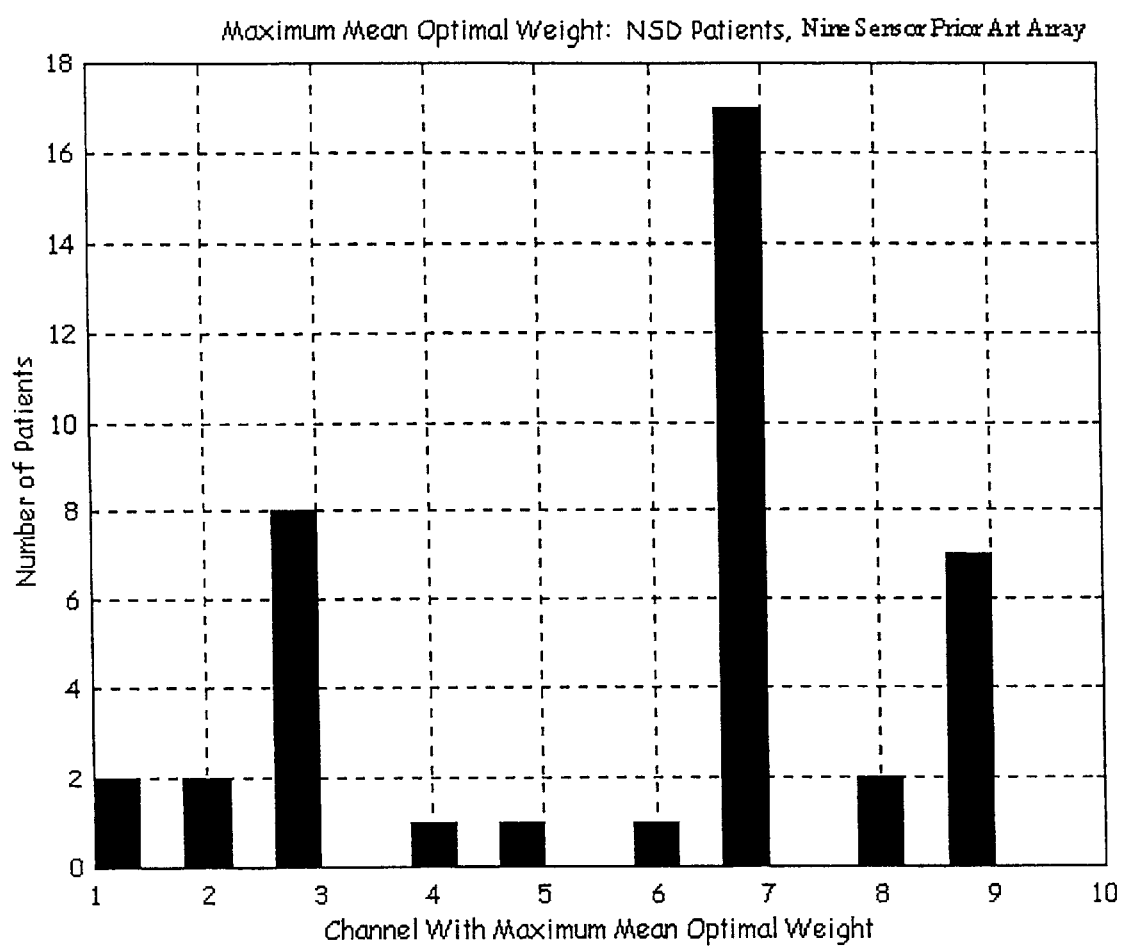
FIG. 5 is a histogram depicting the distribution of channels with maximum channel (highest relative SNR) mean optimal weights. This graph represents only the non-significant disease (NSD) patients (using the FIG. 1 prior art nine-sensor array configuration).
Figure 6:
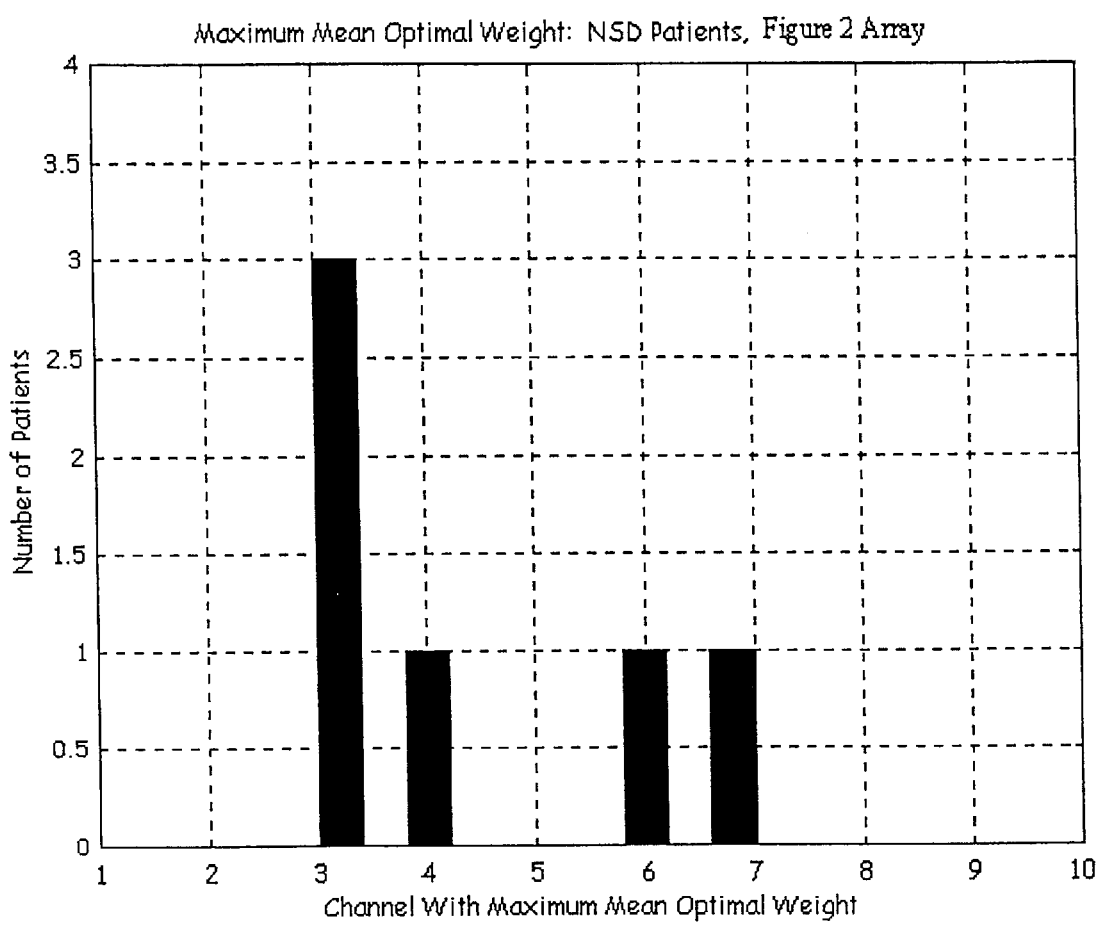
FIG. 6 is a histogram depicting the distribution of channels with maximum mean optimal weight. This graph represents the NSD patients and uses the nine-sensor array configuration of FIG. 2.

FIGS. 1 and 2 grayscale image maps show optimal weights as distributed at the nominal sensor locations for two different nine-sensor array configurations. FIG. 1 illustrates the conventional nine-sensor array (concentric arrangement) of the 20186 application and FIG. 2 illustrates a different nine-sensor array configuration. The channel number and weight are identified according to its sensor location.

The present invention compares the weighted channels to identify the particular channels corresponding to sensors within a multi-channel sensor array which meet a predetermined or relative threshold value. Preferably, the sensor locations of the channels with the three largest weights (or three sensors with one or two of the largest calculated weights) are used to define the acoustic window perimeter. The acoustic window perimeter is drawn to extend and include the sensors corresponding to the three largest weighted channels and may also include sensors corresponding to channels with lesser weighted values, such as shown in FIG. 7. As noted the predetermined threshold value(s) can be an absolute number, i.e., such as those at above about a 0.7 optimal value or a relative threshold such as a sliding scale which is set such that it includes at least three sensors or channels. Accordingly, more than three channels may have relatively high weights and the acoustic window will be drawn to include at least the sensors corresponding to those channels. For example, one channel may have a weighted value of about 0.8 while three channels may have a 0.7 weighted value. In this instance, sensors corresponding to all four channels will be preferably included within the acoustic window.

That is, referring again to FIG. 7, a plurality of increased or relatively high weighted channels (channels 2, 3, 4, 7, 8, 9) are identified (having the top three weighted values of 0.9, 0.7, and 0.5). In order to include the sensors corresponding to these channels, the acoustic window perimeter extends from the sensor locations for channels 2 and 7 on the top to the sensor location for channel 3 on the bottom and over to the sensor locations for channels 8 and 9 and 4 to the patient right and the sensor location for channel 2 on the patient left.

Because the spatial variation of the weights is smooth across the arrays, it is appropriate to consider the channels with the highest weights as indicators of the sensor locations within the bounds of an acoustic window. The channels with the maximum mean (across beats) optimal weights are found and shown in FIGS. 3 through 6 and are drawn within the acoustic window by the broken line perimeter in FIG. 7. FIGS. 1 and 7 show an acoustic window that extends in the x-direction from about 4 cm to about 10 cm below the $2^{nd}$ intercostal space (ICS) and in the y-direction. Sensors to the patient's left are favored. Channels 3 and 4 appear to be close to the $6^{th}$ ICS where the window widens. In FIG. 7, channel 4 is included in the window.

The nine sensors of the sensor array of FIG. 2 are placed in the intercostal spaces. Sensor 1 is placed in the $2^{nd}$ ICS at the left-sternal border, just as it is in the prior art array of FIGS. 1 and 7. The second row (sensors/channels 2 and 3) is placed in the $3^{rd}$ ICS and so on. The results for this FIG. 2 configuration show an acoustic window that covers the area left of the $3^{rd}$ ICS and then follows the sternum covering the $4^{th}$ and $5^{th}$ intercostal spaces.

Combining these results for FIGS. 1 and 2 yields an acoustic window that starts at the left of the $3^{rd}$ ICS and then follows the sternum covering the $4^{th}$ through $6^{th}$ spaces, widening to the right at the $6^{th}$ space. This is the window is visualized by the superposed broken lines in FIG. 7.

In the nine-sensor array of the 20186 application (FIGS. 1, 5 and 7), two modes appear in the histograms: one at channels 7, 8, and 9 and a second at channels 2, 3, and 4. These modes are relatively unchanged when the analysis is done for interventional and non-significant disease patients. See FIGS. 3 and 4. For the FIG. 2 array, modes appear at channels 3 and 4 and at channels 6 and 7. All of these patients were normal or non-significant diseased patients.

Because the relative (preferably optimal) SNR channel weights are independent of the types or sizes of sensors, the present invention may allow for acoustic window visualization without regard to sizes or types of sensors used. One embodiment of the invention provides acoustic window visualization by use of any piezoelectric film, e.g., polyvinylidene difluoride or PVDF sensors. Useful PVDF sensors are described in commonly assigned U.S. patent application Ser. No. 09/136,933 filed Aug. 20, 1998 and U.S. Provisional Application Ser. No. 60/132,041 filed Apr. 30, 1999. The contents of these applications are hereby incorporated by reference as if recited in full herein. Other embodiments of the invention include acoustic window visualization by use of commercial seismic or medical accelerometers available from Wilcoxon Research, 21 Firstfield Road, Gaithersburg, Md. 20878 or piezoelectric film sensors available from MSI (formerly AMP Incorporated), 449 Eisenhower Boulevard, Harrisburg, Pa. 17111-2302.

The data reported in this application was obtained with arrays of commercial Wilcoxon accelerometers. Appendix A describes a suitable method for weighting sensor channels using SNR values of a multi-channel sensor array. Of course, alternate SNR evaluations can also be used.

In operation, the acoustic window of a person is preferably determined in conjunction with an acoustic-based non-invasive diagnostic evaluation, based on the following method steps. Alternatively, the acoustic window can be statistically defined by correlation of measurements for each array geometry of interest according to the following method steps across a population of patients. If the latter, the population based acoustic window determination can be used to define a preferred array geometry (one having improved SNR channels, by sizing and configuring the location of the sensors and the array geometry itself to fit substantially within the computationally-identified and correlated acoustic window). In addition, the methods of the present invention can be used to define additional correlation and a corresponding set of multi-sensor array configurations to allow for further customized clinical applications. For example the acoustic window and preferred array configuration and size can be defined and classified corresponding to height, weight, chest size, and/or gender to further customize sensor array geometry particularly suitable within target patient groups.

Figure 8:
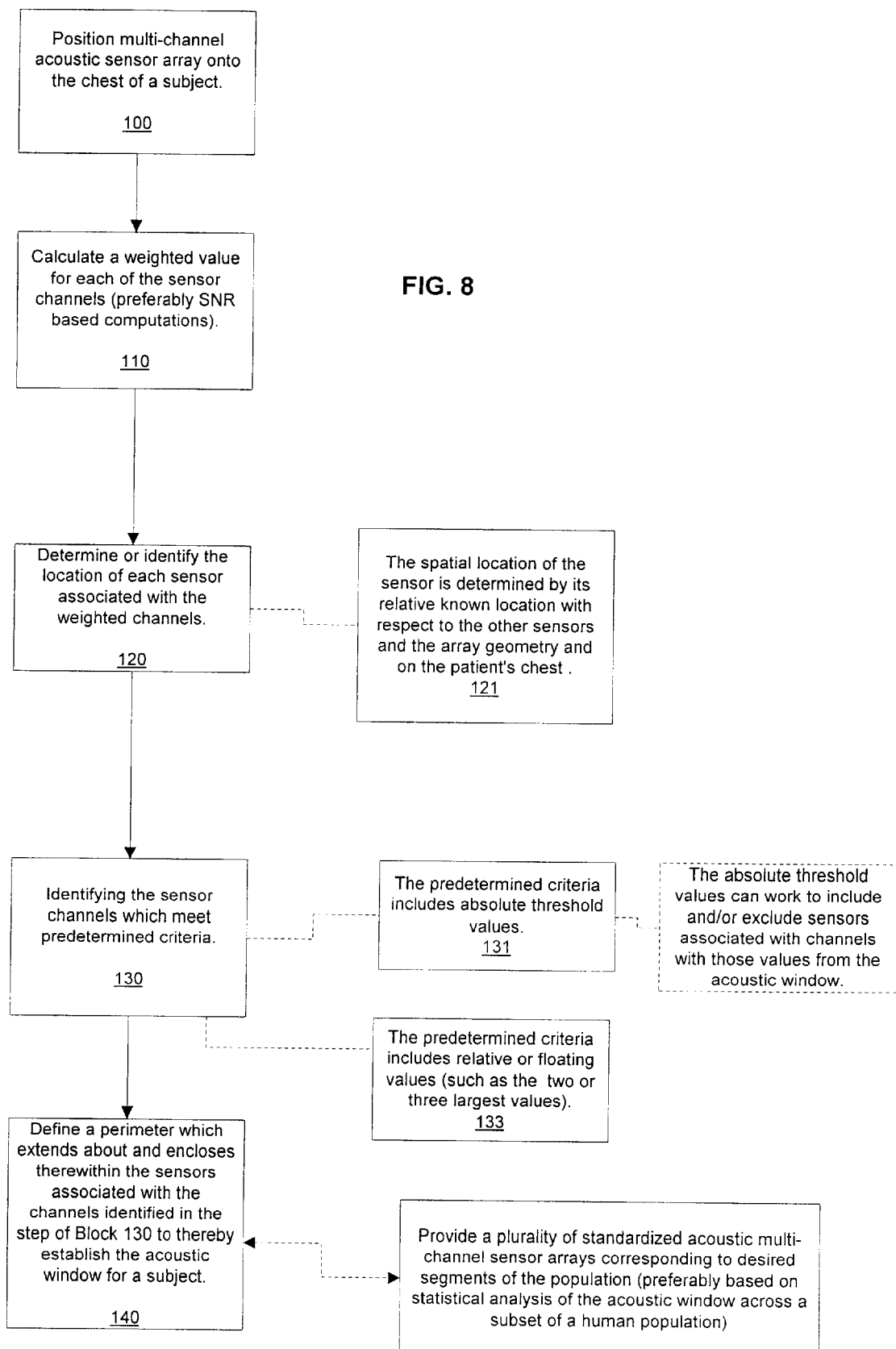
FIG. 8 is a block diagram of method steps used to determine an acoustic window according to the present invention.

Referring to FIG. 8, a multi-channel sensor array is positioned onto the chest of a subject undergoing evaluation (Block 100). A plurality of weighted-values are calculated, one for each of the sensor channels in the multi-channel sensor array (Block 110). The weights are associated with the SNR values of each signal for each channel. Preferably, the SNR-based weighted values are computationally scaled to an estimated SNR and mapped (electronically). In addition, the position or spatial location of each channel is identified (Block 120). Preferably, the position is identified relative to its location within a substantially fixed (known geometric) configuration multi-channel sensor array (Block 121). The position can also be otherwise established, such as by identifying each sensor position relative to a spatial axis or grid system and/or relative to a particular ICS/chest location. However established, the relative location of one sensor to another sensor in the sensor array may be utilized to define an acoustic window with respect to other sensors in the array according to the present invention. It is also preferred that the sensor array be substantially consistently positioned on the chest within an estimated acoustic window across different subjects and/or on the same subject in subsequent procedures.

For each known geometrical relatively constant array configuration, the relative position of each sensor within that array can be electronically represented and identified by mapping the known spatial relationship between the location of each sensor to the others. Further, over a population of subjects, a statistical correlation of the size and shape of the acoustic window (based on number of high SNR weights/channels) as it relates to a particular array configuration can be used to size and configure the array to positively affect the diagnostic operation of the sensors. As such, a set of differently sized array geometries can be provided to correspond thereto (to a particular population segment) to allow a clinician easy access to different sizes at the point of application. For example two or three different acoustic sensor arrays having the same or different geometries and sized (preferably larger and smaller) can be provided to correspond with the subject's actual anatomical considerations (typically the anatomical considerations will correspond with demographic or physical factors such as bone structure/dimensions, patient's height, weight, gender, age, position, etc.). Of course, the receiver and signal processor can be programmed to recognize the selected array to provide for signal correlation.

Alternatively, or in addition to the improved sizing of the array, the method can be used to define which channels are "active" during diagnostic listening corresponding to the high-weight channels or channels located within the acoustic window at the time of the procedure. (The acoustic window may be statistically consistent across a particular population, but accurate or repeatable positioning may vary procedure to procedure). Thus, this method, if performed contemporaneously, may provide additional improvements in diagnostic capabilities. In any event, it is preferred that the array comprises at least four sensors and a corresponding four channels.

Next, the sensor channel weights which meet predetermined criteria are identified (Block 130). This predetermined criteria can include one or both of absolute or relative criteria. For example, establishing a minimum threshold weight value and identifying which sensors have weighted values which meet or exceed the minimum threshold values (and/or identifying and subsequently excluding those that fail to meet minimum values) (Block 131). Alternatively, or in addition to the absolute criteria, relative or floating criteria can be employed (Block 133). For example, identifying the sensor(s) having the three largest weighted values. As another relative example, the method may identify the largest weighted value calculated and then count the number of sensors associated with channels exhibiting this value. If the number of sensors for channels having this value is less than three, then the next largest value is identified and the number of sensors associated with these channels having this value are counted, etc. This procedure can be repeated until a desired number of the sensors within the multi-sensor array are identified (preferably at least three sensors). Of course, combinations of absolute and relative test criteria can also be employed. Preferably, less than all of the sensors in the array are identified by the predetermined test criteria evaluation (i.e., at least three, but less than all of the sensor channels will typically correspond to the sensor channels determined to have high (and preferably optimal) weights).

It is also possible to establish the predetermined test criteria to identify any channel which should be excluded from consideration during diagnostic procedures based on its failure to meet certain minimum threshold criteria (increased signal interference or those channels exhibiting low weighted values) to thereby exclude sensors corresponding to channels which may be blocked by the presence of undesirable acoustic path interference (such as that associated with lung tissue) within the chest area. This method can be performed independent of or in addition to the increased or high-weight value method described above.

Based on the (high-weight) sensor channels identified by the predetermined test criteria evaluation step, a perimeter can be defined to extend about and enclose the sensors corresponding to channels meeting the predetermined criteria, thereby defining an acoustic window region on the chest of a subject (Block 140). That is, at least figuratively, a perimeter line can be drawn (electronically) about the sensor locations (which correspond to chest locations) which exhibit the high-weight values to define the bounds or outer limits of an area or region on the subject's chest corresponding to the acoustic window.

Preferably, the multi-channel sensor array has a perimeter and an associated aperture (the overall size of the array) and the array is configured such that the perimeter of the sensor array substantially conforms to (and/or extends beyond) the bounds of an acoustic window that starts at the left of the third intercostal space, follows the sternum covering the fourth through six intercostal spaces, and widens to the right at the sixth intercostal space of a person.

It will be understood that each of the method steps, block diagrams (or blocks in a flowchart illustration), and combinations of blocks in flowchart illustrations or blocks in block diagram figures), can be implemented by computer program instructions. These computer program instructions may be loaded onto a computer or other programmable data processing apparatus to produce a machine, such that the instructions which execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce computer implemented process such that the instructions which execute on the computer or other programmable apparatus provide steps for implementing the functions specified in the flowchart block or blocks and/or block diagrams.

Accordingly, the method steps, blocks of the block diagrams or in a flowchart illustration support combinations of means for performing the specified functions and program instruction means for performing the specified functions. It will also be understood that each block of the block diagram or flowchart illustrations, and combinations of blocks in the block diagrams or flowchart illustrations, can be implemented by special purpose hardware-based computer systems which perform the specified functions or steps, or combinations of special purpose hardware and computer instructions.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clause are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

APPENDIX A

To determine the optimal weights for summing the channels together let $R_{S/N}$ be the ratio of signal to noise. The signals, if time aligned will sum coherently by the magnitude of the weights, while the noise will sum incoherently as the square-root of the sum of the squares of the noise in each channel times its respective weight. The equation becomes the ratio of these two relations. For the case of four channels:

$$R_{\frac{S}{N}} = \frac{w_1 S_1 + w_2 S_2 + w_3 S_3 + w_4 S_4}{[[w_1 N_1]^2 + [w_2 N_2]^2 + [w_3 N_3]^2 + [w_4 N_4]^2]^{\frac{1}{2}}}$$

where:

$S_i$=signal on the ith channel, $N_i$=noise on the ith channel (white and orthogonal to the noise and the signals on the other channels, and $w_i$=real valued weight for ith channel.

The maximum can be found by taking the partial derivatives of the signal to noise ratio with respect to the weights and setting them equal to zero. The four partial derivatives are shown below.

$$\frac{\partial R_{\frac{S}{N}}}{\partial w_1} = \frac{\partial R_{\frac{S}{N}}}{\partial w_2} = \frac{\partial R_{\frac{S}{N}}}{\partial w_3} = \frac{\partial R_{\frac{S}{N}}}{\partial w_4} = 0$$

$$\frac{\partial R_{\frac{S}{N}}}{\partial w_1} = \frac{S_1}{[[w_1N_1]^2+[w_2N_2]^2+[w_3N_3]^2+[w_4N_4]^2]^{\frac{1}{2}}} - \frac{[w_1S_1+w_2S_2+w_3S_3+w_4S_4]w_1N_1^2}{[[w_1N_1]^2+[w_2N_2]^2+[w_3N_3]^2+[w_4N_4]^2]^{\frac{3}{2}}}$$

$$\frac{\partial R_{\frac{S}{N}}}{\partial w_2} = \frac{S_2}{[[w_1N_1]^2+[w_2N_2]^2+[w_3N_3]^2+[w_4N_4]^2]^{\frac{1}{2}}} - \frac{[w_1S_1+w_2S_2+w_3S_3+w_4S_4]w_2N_2^2}{[[w_1N_1]^2+[w_2N_2]^2+[w_3N_3]^2+[w_4N_4]^2]^{\frac{3}{2}}}$$

$$\frac{\partial R_{\frac{S}{N}}}{\partial w_3} = \frac{S_3}{[[w_1N_1]^2+[w_2N_2]^2+[w_3N_3]^2+[w_4N_4]^2]^{\frac{1}{2}}} - \frac{[w_1S_1+w_2S_2+w_3S_3+w_4S_4]w_3N_3^2}{[[w_1N_1]^2+[w_2N_2]^2+[w_3N_3]^2+[w_4N_4]^2]^{\frac{3}{2}}}$$

$$\frac{\partial R_{\frac{S}{N}}}{\partial w_4} = \frac{S_4}{[[w_1N_1]^2+[w_2N_2]^2+[w_3N_3]^2+[w_4N_4]^2]^{\frac{1}{2}}} - \frac{[w_1S_1+w_2S_2+w_3S_3+w_4S_4]w_4N_4^2}{[[w_1N_1]^2+[w_2N_2]^2+[w_3N_3]^2+[w_4N_4]^2]^{\frac{3}{2}}}$$

Multiplying the first term in these equations by one, written as:

$$\frac{[[w_1N_1]^2+[w_2N_2]^2+[w_3N_3]^2+[w_4N_4]^2]}{[[w_1N_1]^2+[w_2N_2]^2+[w_3N_3]^2+[w_4N_4]^2]}$$

and setting them equal to zero and simplifying yields:

$$w_1\frac{N_1^2}{S_1} = \frac{[[w_1N_1]^2+[w_2N_2]^2+[w_3N_3]^2+[w_4N_4]^2]}{w_1S_1+w_2S_2+w_3S_3+w_4S_4}$$

$$w_2\frac{N_2^2}{S_2} = \frac{[[w_1N_1]^2+[w_2N_2]^2+[w_3N_3]^2+[w_4N_4]^2]}{w_1S_1+w_2S_2+w_3S_3+w_4S_4}$$

$$w_3\frac{N_3^2}{S_3} = \frac{[[w_1N_1]^2+[w_2N_2]^2+[w_3N_3]^2+[w_4N_4]^2]}{w_1S_1+w_2S_2+w_3S_3+w_4S_4}$$

$$w_4\frac{N_4^2}{S_4} = \frac{[[w_1N_1]^2+[w_2N_2]^2+[w_3N_3]^2+[w_4N_4]^2]}{w_1S_1+w_2S_2+w_3S_3+w_4S_4}$$

For these equations to go to zero, the numerators must go to zero, which yields the following relationships:

$$w_1\frac{N_1^2}{S_1} = w_2\frac{N_2^2}{S_2} = w_3\frac{N_3^2}{S_3} = w_4\frac{N_4^2}{S_4}$$

If a priori information exists on the S and N of each channel then let $w_1=1$, then the other weights can be found. If the S and N for each channel must be found a postori, then the correlation coefficients can used to generate estimates of S and N for each channel. The matrix of peak correlation values between channels must be found to do the time alignment. By the following method, the column or row of the peak values of the cross correlation matrix that, when summed has the greatest value, is the preferred reference channel. The correlation values to be used are those between this reference channel and the other channels.

If we think of the signal and noise as vectors, this diagram illustrates their relationship when the noise is orthogonal to the signal.

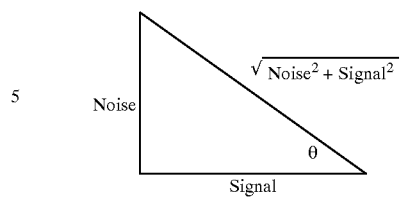

From the diagram, we can write the SNR as.

$$SNR = \frac{\text{Signal}}{\text{Noise}} = \frac{1}{\tan(\theta)} = \frac{\cos(\theta)}{\sin(\theta)}$$

We assume the peak correlation between two channels goes as $\rho = \cos(\theta)$. This means that when two channels are perfectly correlated, $\rho=1$. This happens when there is no noise, or $\rho=0$ and the SNR is infinite. Then we can write the SNR in terms of $\rho$, the peak correlation between channels:

$$SNR = \frac{\rho}{\sqrt{1-\rho^2}}$$

We cannot use this estimate for the reference channel because its correlation with itself is $\rho=1$, which gives infinite SNR. Instead, we use the peak correlation value between the reference and the channel with the highest correlation with the reference. The weight for the reference channel is then set to $\omega=1$. The weights of each other channel are set proportionally, according to the relationship derived previously of its SNR to the reference channel SNR. Finally, the acoustic signals from the n channels are combined using the weighted sum:

$$y = \sum_{i=1}^{n} \omega_i x_i$$

where:
y=optimally weighted sum of the channels,
$x_i$=measurement from ith channel,
$\omega$=weight for ith channel.

This method allows an estimate of the beamformer output without reference to a particular location in space. In addition, by using the lags found before an intervention with the sensors at the same physical locations after an intervention, the beam can look at the same location as before the intervention without knowing specifically where it is. There is no requirement for knowledge of the velocity in the media. A similar method can be developed for the frequency domain. The conventional beamformer output is a Rayleigh quotient. The steering vector that will produce the greatest output is the first eigenvector of the R matrix and its value is the first eigenvalue of the R matrix:

Then the output of the beam former is:
$S=eV_1$, is the first eigenvector of the R matrix.
Then the output of the beam former is:

$$B_{\text{output in power}} = \frac{eV_1^H ReV_1}{eV_1^H eV_1} = \sigma_1$$

So the maximum output of the beamformer can be determined with out knowledge of the velocities in the media. The eigenvector can be saved and after intervention if the sensors are in the same place. It can be used to steer the beam to where the maximum output was previously. Since there are as many R matrices as frequencies of interest a plot of the first or dominate eigen values vs. frequency gives an eigen spectrum, which is the magnitude of the sum of the correlated parts of the channels at each frequency.

I claim:

1. A method for determining an acoustic window suitable for passive-acoustic coronary artery disease evaluation, comprising the steps of:

(a) positioning a multi-channel acoustic sensor array onto the chest of a subject;

(b) calculating a weighted signal value for each of the sensor channels in the multi-channel sensor array;

(c) determining the location of each sensor corresponding to the sensor channel in the array;

(d) identifying the sensor channels which meet predetermined test criteria; and (e) defining a perimeter which substantially extends about and encloses therewithin the sensors associated with the sensor channels identified in step (d), thereby defining an acoustic window suitable for acoustic listening diagnostic procedures.

2. The method according to claim 1, wherein said multi-channel sensor array comprises at least four separate sensors and a corresponding number of sensor channels.

3. The method according to claim 1, wherein said calculating step is performed by assigning SNR based weighted values to each of the sensor channels.

4. The method according to claim 1, wherein the predetermined test criteria includes absolute criteria.

5. The method according to claim 4, wherein the absolute criteria comprises predetermined minimum threshold values.

6. The method according to claim 1, wherein the predetermined test criteria includes relative criteria.

7. The method according to claim 6, wherein the relative criteria includes identifying the sensors corresponding to the sensor channels having the three highest weight values.

8. The method according to claim 2, wherein the predetermined test criteria is defined such that it identifies at least three sensors.

9. The method according to claim 1, wherein the predetermined test criteria comprises identifying channels exhibiting weight values below a minimum value.

10. The method according to claim 1, wherein the acoustic window is drawn to include a subset of the sensors in the multi-channel sensor array.

11. The method according to claim 1, wherein the method is repeated across a population of subjects, and wherein the location of the sensors associated with the sensor channels identified in step (d) are correlated across the population to define a standardized acoustic window representation.

12. The method according to claim 11, further comprising the step of configuring at least one standardized multi-channel acoustic sensor array having at least four sensors and a known geometric configuration such that its sensors are positioned substantially within the standardized acoustic window representation.

13. The method according to claim 12, wherein the multi-channel acoustic sensor array comprises greater than four sensors, and wherein said array has a perimeter and an aperture and wherein said array perimeter substantially conforms to the perimeter that defines the acoustic window suitable for acoustic listening diagnostic procedures.

14. The method according to claim 13, wherein the array and acoustic window perimeter is configured such that it extends about the left of the third intercostal space, follows the sternum covering the fourth through six intercostal spaces, and widens to the right at the sixth intercostal space of a person.

* * * * *